United States Patent
Van Zijl et al.

(10) Patent No.: US 10,180,478 B2
(45) Date of Patent: Jan. 15, 2019

(54) MAGNETIC RESONANCE SYSTEM AND METHOD FOR DETECTING THE BUILDUP OF THE TRANSFER OF CHANGES IN MAGNETIZATION FROM NUCLEI IN MOBILE SOLUTE MOLECULES IN TISSUE

(71) Applicants: THE JOHNS HOPKINS UNIVERSITY, Baltimore, MD (US); KENNEDY KRIEGER INSTITUTE, INC., Baltimore, MD (US)

(72) Inventors: Peter Van Zijl, Ellicott City, MD (US); Jiadi Xu, Lutherville, MD (US); Nirbhay Yadav, Baltimore, MD (US)

(73) Assignees: The Johns Hopkins University, Baltimore, MD (US); Kennedy Krieger Institute, Inc., Baltimore, MD (US)

( * ) Notice: Subject to any disclaimer, the term of this patent is extended or adjusted under 35 U.S.C. 154(b) by 510 days.

(21) Appl. No.: 14/774,721

(22) PCT Filed: Mar. 12, 2014

(86) PCT No.: PCT/US2014/024248
§ 371 (c)(1),
(2) Date: Sep. 11, 2015

(87) PCT Pub. No.: WO2014/165051
PCT Pub. Date: Oct. 9, 2014

(65) Prior Publication Data
US 2016/0018496 A1    Jan. 21, 2016

Related U.S. Application Data

(60) Provisional application No. 61/777,191, filed on Mar. 12, 2013.

(51) Int. Cl.
G01R 33/56    (2006.01)
G01R 33/48    (2006.01)
(Continued)

(52) U.S. Cl.
CPC .......... *G01R 33/5605* (2013.01); *A61B 5/055* (2013.01); *A61B 5/14539* (2013.01);
(Continued)

(58) Field of Classification Search
None
See application file for complete search history.

(56) References Cited

U.S. PATENT DOCUMENTS

2011/0054299 A1    3/2011    Ling et al.
2012/0019245 A1    1/2012    Reddy et al.
(Continued)

FOREIGN PATENT DOCUMENTS

WO    2011-091365 A1    7/2011

*Primary Examiner* — Jermele M Hollington
(74) *Attorney, Agent, or Firm* — Johns Hopkins Technology Ventures

(57) ABSTRACT

An embodiment in accordance with the present invention provides a new MRI method to image the buildup of exchange transfer processes from nuclei in mobile solute molecules in tissue via another molecule (e.g. solvent such as water). The pulse sequence can detect Chemical Exchange Saturation Transfer (CEST), relayed Nuclear Overhauser Enhancement (rNOE) CEST, and selective induced exchange transfer processes. Further, the proposed MRI pulse sequence involves acquiring two or more images with a difference in waiting period (delay) after a radiofrequency excitation, saturation pulse, or series of such pulses. This produces a series of exchange transfer images sensitive to the speed of transfer of changes in magnetization. Subtracting two images or fitting a time series produces maps with minimum interference from direct water saturation and from semi-solid magnetization transfer and other fast exchanging protons.

24 Claims, 10 Drawing Sheets

(51) Int. Cl.
- *A61B 5/055* (2006.01)
- *G01R 33/46* (2006.01)
- *A61B 5/145* (2006.01)
- *G01N 24/08* (2006.01)
- *G01R 33/465* (2006.01)

(52) U.S. Cl.
CPC ..... *G01R 33/4608* (2013.01); *G01R 33/4828* (2013.01); *G01N 24/08* (2013.01); *G01R 33/465* (2013.01)

(56) References Cited

U.S. PATENT DOCUMENTS

| | | |
|---|---|---|
| 2012/0041299 A1 | 2/2012 | Kassai et al. |
| 2012/0289818 A1 | 11/2012 | Van Zijl et al. |

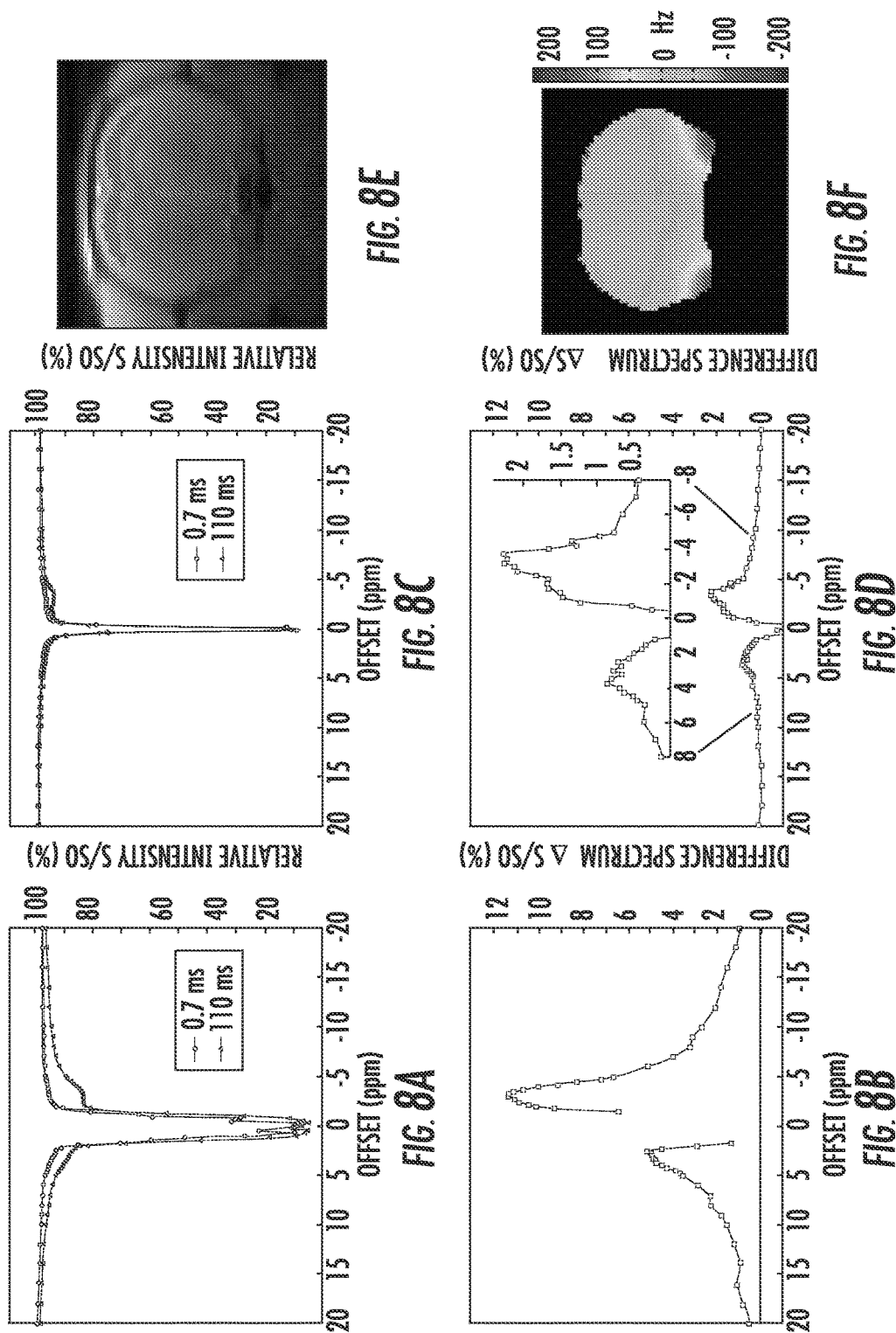

MAGNETIC RESONANCE SYSTEM AND METHOD FOR DETECTING THE BUILDUP OF THE TRANSFER OF CHANGES IN MAGNETIZATION FROM NUCLEI IN MOBILE SOLUTE MOLECULES IN TISSUE

CROSS-REFERENCE TO RELATED APPLICATIONS

This application is a 35 U.S.C. § 371 U.S. national entry of International Application PCT/US2014/024248, having an international filing date of Mar. 12, 2014, which claims the benefit of U.S. Provisional Application No. 61/777,191, filed Mar. 12, 2013, the content of each of the aforementioned applications is herein incorporated by reference in their entirety.

GOVERNMENT SUPPORT

This invention was made with government support under NIH/NIBIB RO1 EB015032 awarded by the National Institutes of Health. The government has certain rights in the invention.

FIELD OF THE INVENTION

The present invention relates generally to imaging. More particularly the present invention relates to a system and method for magnetic resonance imaging.

BACKGROUND OF THE INVENTION

CEST imaging has developed into a powerful technology with widespread interest in the MRI community. CEST imaging utilizes radiofrequency (RF) irradiation to selectively saturate solute protons. The saturation is transferred to water through rapid exchange of these protons, resulting in a reduction in water signal intensity. If the exchange rate is sufficiently fast (residence time in millisecond range) and the irradiation period sufficiently long (seconds range), the low concentration saturated solute protons are mostly replaced by high concentration unsaturated water protons so that the saturation transfer process repeats many times during the course of the RF irradiation. Consequently, the selective irradiation of these solute protons can have a discernable effect on the water signal intensity, which allows the indirect imaging of low concentration solutes through water. Furthermore, the dependence of the CEST effect on the RF irradiation duration ($t_{sat}$) and strength ($B_1$) provides additional information on the kinetics of exchange, pH, the concentration of the exchangeable protons, and the relaxation properties of water. This possibility to enhance sensitivity has led to a large variety of techniques developed for imaging low concentration diamagnetic compounds, such as Glycosoaminoglycans, Glucose/Glycogen, Glutamate, amino acids, peptides and proteins, as well as paramagnetic lanthanide complexes (PARACEST) and particles.

Among all the CEST techniques, the amide proton transfer (APT) approach, which targets the exchangeable amide protons in peptides and proteins, has become of particular interest because of several unique properties that make it favorable for in vivo application in the clinic. These include (i) the high total concentration of amide protons of endogenous mobile proteins and peptides, corresponding to about 70 mM amide proton concentration found in the mammalian brain; (ii) sufficiently low interference from the water signal due to a relatively large chemical shift between amide and water protons (~3.6 ppm); (iii) the relatively slow exchange rate (~30 Hz) of these amide protons that allows use of low power RF saturation pulses for their detection. To date, APT has been successfully applied to detect tumors in the brain, prostate, and breast in vivo in patients, and pH changes during ischemia in vivo in preclinical models.

In APT imaging, loss of signal can result from a number of competing mechanisms such as direct water saturation (DS), and conventional magnetization transfer contrast (MTC) from semi-solid macromolecules to water. CEST/APT experiments therefore generally require acquisition of a series of images as a function of irradiation frequency (Z-spectrum). This is followed by asymmetry analysis of the Z spectrum with respect to the water proton frequency, in which the magnetization transfer ratio (MTR) obtained at the negative offset with respect to water is subtracted from the MTR at the corresponding positive offset. While the goal of this approach originally was to remove the effects of DS and MTC, many investigators now realize that complete removal of MTC may not be possible in vivo, because MTC contrast is not completely symmetric about the water signal. In addition to MTC, it has been shown recently that contrast in Z-spectra also arises through indirect transfer of saturation induced nuclear Overhauser enhancements (NOEs) in mobile macromolecules between aliphatic/olefinic or aromatic protons and exchangeable protons, which then transfer to water (relayed transfers). Most of this signal is upfield from water (lower frequency), where the aliphatic and olefinic protons resonate. This relayed CEST contrast is a two-stage process. First, nonexchangeable protons transfer their saturation-induced Nuclear Overhauser Enhancement (NOE) via through-space dipolar coupling, and then the saturated magnetization is transferred to the water pool, most likely by chemical exchange as known from studies of the inverse exchange-relayed process in protein solution and in vivo. Notice that, contrary to the semisolid MTC effect, direct dipolar exchange through space is unlikely to occur in mobile proteins as that process is known to be much slower than exchange. This type of contrast will be referred to as "relayed-NOE CEST" (rNOE-CEST) to distinguish it from direct exchange contrast. This rNOE-CEST shares many properties with the APT contrast, but in principle has much stronger signal due to the large amount of aliphatic protons compared to amide protons. Therefore it has great potential for in vivo application.

The acquisition of detailed Z-spectra is time consuming. In addition, extra scans are often performed (e.g., water saturation shift referencing, WASSR) to allow for a voxel-based correction of the water proton frequency used as reference in the asymmetry analysis. The need to acquire Z-spectra and WASSR-spectra poses a significant practical limitation for clinical translation of APT studies, because more signal averaging could take place (to enhance sensitivity) or the experiment time could be reduced if less frequencies were needed. Recently, faster methods have been suggested, including SAFARI, employing a frequency-alternating scheme requiring four acquisitions and CERT, using two rotations, requiring only two acquisitions.

It would therefore be advantageous to provide a system and method for obtaining APT and rNOE-CEST images that provides the same results in a shorter amount of time.

SUMMARY OF THE INVENTION

The foregoing needs are met, to a great extent, by the present invention, wherein in one aspect a method for detecting the buildup of exchange transfer processes from nuclei in endogenous or exogenous mobile solute molecules in tissue using magnetic resonance (MR) imaging includes at least two consecutive steps of applying a series (one or more) radiofrequency pulses to change the magnetization of one or more MR sensitive nuclei in these mobile solute molecules and waiting a period after each pulse for transfer of the magnetization change to another molecule, in which the waiting period differs between the two steps. The difference MR signal between the applications of the pulses with different waiting period detected for this another molecule (generally water or a solvent, but other molecules or solutes also possible) reflects the concentration of the original mobile solute molecules.

In accordance with an aspect of the present invention, the mobile molecules are characterized by having a finite linewidth, i.e. excluding semi-solid molecules studied in conventional magnetization transfer contrast (MTC). The radiofrequency pulse is a frequency-selective excitation pulse for the chemical shift(s) of the nuclei of interest. The radiofrequency pulse can also be a frequency-selective saturation pulse for the chemical shift(s) of the MR sensitive nuclei. The MR sensitive nucleus can be any nucleus that has spin and thus is detectible with magnetic resonance, for instance 1H, 13C, 31P, 23Na, and all nuclei used for NMR and MRI. The period for waiting after each pulse is as short as 0 ms for the first step and can range from 1 to several hundred ms for the repeated step or steps of application of the multi-pulse radiofrequency pulse sequence.

In accordance with another aspect of the present invention, the transfer of the magnetization change occurs directly via chemical exchange after labeling of an exchangeable nucleus, or the transfer of the magnetization change occurs in a relayed fashion via the magnetization of other nuclei in the molecule. Alternately, the transfer of the magnetization change occurs via exchange of a multi-atomic entity containing a labeled magnetic nucleus or nuclei via other nuclei. The another molecule can be a solvent or a solute.

In accordance with still another aspect of the present invention, the repeating of the pulse sequence is at least once. The waiting a period and waiting a different period can include one or more different repeats. A change in magnitude of the magnetization transfer can be studied as a function of waiting time after the radiofrequency pulses or by taking the difference between different waiting times. The mobile species are endogenous or exogenous peptides, proteins, carbohydrates, nucleic acids, metabolites or exogenous contrast agents. The transfer of the magnetization change occurs directly via chemical exchange or in a relayed fashion via nuclear Overhauser enhancement (NOE) or dipolar transfer. The change in magnitude is used to determine magnetization transfer rates or exchange transfer rates of the nuclei or molecular moieties involved. Additionally, the change in magnitude may be used to monitor pH of the tissue. A magnetic resonance processor can be set up to process and display the waiting time dependent signals and the changes therein.

In accordance with yet another aspect of the present invention, the method can further include acquiring magnetization changes as a function of waiting time at multiple frequencies. Also, the method can include studying the change in magnitude of the magnetization transfer at each of the multiple frequencies as a function of waiting time after the radiofrequency pulse or by taking the difference between different waiting times. The time-dependent magnetization difference can be compared between different frequencies or studied as a function of frequency.

In accordance with another aspect of the present invention, a non-transitory computer readable medium is programmed with elements including applying the radiofrequency pulses with different time delays and applying the time-dependent pulse sequence at multiple selective frequencies. The computer is also programmed to analyze the difference in magnetization change as a function of waiting time and generate images of the differences in magnetization change as a function of waiting time. Different images of the images acquired of the differences in magnetization change as a function of frequency can also be generated using the computer.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 8A-8F illustrate mixing-time dependent Z-spectra for rat brain cortex recorded using 8 Gaussian inversion pulses with $B_1$ levels of 12 μT (2.3 ms length, 8 pulses), as illustrated in FIG. 8A and 2 μT (13.8 ms length, 8 pulses), as illustrated in FIG. 8C. FIGS. 8B and D illustrate plots of the corresponding VDMP-CEST difference spectra.

FIG. 8E illustrates the rat brain ROI from which the Z-spectra were obtained. FIG. 8F illustrates a typical $B_0$ map recorded using the WASSR sequence. The $B_0$ imhomogeneity is less than 150 Hz over the whole brain slice.

DETAILED DESCRIPTION

Figure 1A:
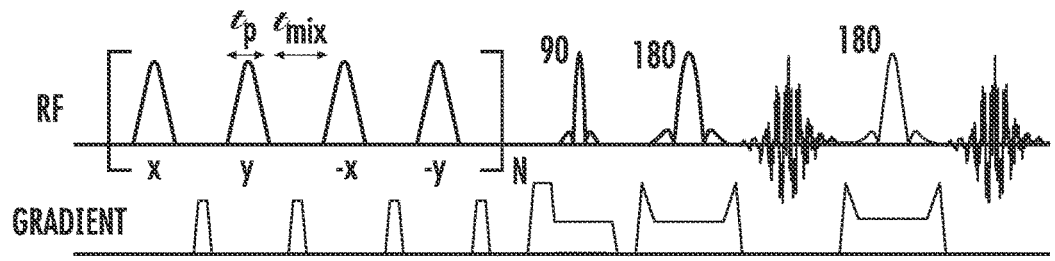
FIG. 1A illustrates a general variable-delay-multi-pulse (VDMP) chemical exchange saturation transfer (CEST) sequence composed of a series (one or more) radiofrequency pulses, in this case a train of Gaussian 180° pulses followed by an MRI readout (here a multi-spin echo sequence) that can be used to implement the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a new MRI pulse sequence to image the transfer of changes in magnetization from nuclei in mobile solute molecules in tissue. The pulse sequence can take the form of a Chemical Exchange Saturation Transfer (CEST), relayed Nuclear Overhauser Enhancement (rNOE) CEST, and frequency selective pulse induced exchange transfer. Further, the proposed pulse sequence involves acquiring two or more images with a difference in waiting period (delay time or mixing time) after a radiofrequency excitation pulse, saturation pulse, or series of such pulses. This produces a series of exchange transfer images sensitive to the speed of transfer of changes in magnetization. Subtracting two images or fitting a time series produces maps with minimum interference from direct water saturation and from semi-solid magnetization transfer and other fast exchanging protons.

Briefly, the magnetic resonance method includes applying a series of radiofrequency pulses to change the magnetization of one or more MR sensitive nuclei in mobile solute molecules and waiting a period after each pulse for transfer of the magnetization change to another molecule. The method also includes detecting this another molecule using MR imaging or spectroscopy and repeating the applying one or more radiofrequency pulses to change the magnetization of one or more MR sensitive nuclei in these mobile solute molecules. In this repeat, a different waiting period is used after each pulse for transfer of the magnetization change to this another molecule, and the another molecule can be detected using MR imaging or spectroscopy. Additionally, the difference MR signal is determined for the another molecule between the applications of the pulses with different waiting period. It should be noted that the method can be carried out controlled by a computer, a non-transitory computer readable medium loaded onto a server or processor in wired or wireless network communication with the MR imaging system, or using any other suitable computer control device to steer MR scanners known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

Figure 1B:
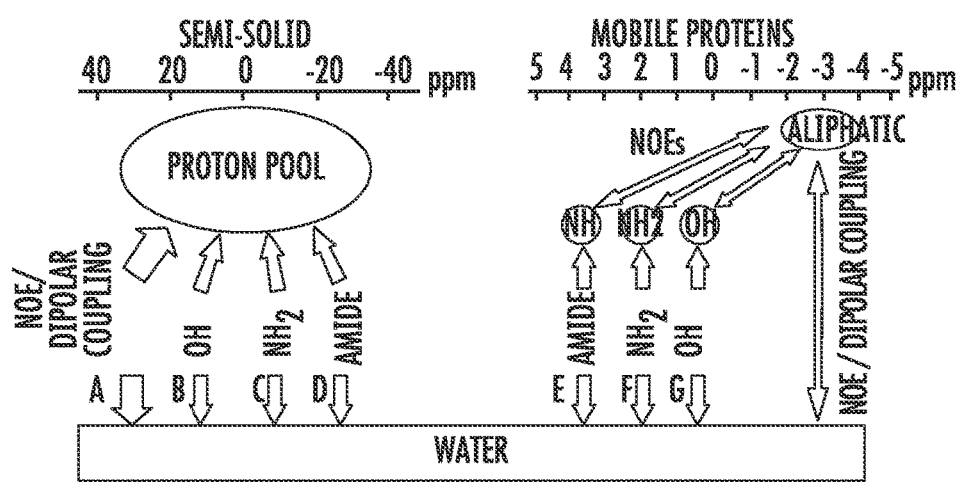
FIG. 1B illustrates possible pathways of magnetization transfer in semi-solid macromolecules and mobile proteins/peptides.

More particularly, the method of the present invention provides for obtaining APT, CEST, and/or rNOE-CEST contrast images using a Variable Delay Multi-Pulse CEST (VDMP-CEST) sequence. This scheme is based on varying the delay (mixing time) between the RF pulses in a pulsed RF irradiation scheme, as illustrated in FIG. 1A. At least one irradiation frequency is used and at least two images with different delay times need to be acquired at this frequency, with the first image collected with delay equal to zero or the minimum time possible on the scanner (reference image) and the second with a delay set to a value sufficient for weighting the images based on the appropriate magnetization transfer rate. The final VDMP-CEST image is then obtained by subtracting the long delay image from the reference image or vice versa. FIG. 1A illustrates the VDMP-CEST sequence composed of a train of Gaussian 180° pulses followed by an MRI readout (here a multi-spin echo sequence, but it could be any readout). The pulse width is $t_p$ and the inter pulse delay $t_{mix}$. CYCLOPS phase cycling of the 180° pulses is applied together with crusher gradients during $t_{mix}$ to suppress residual transverse magnetization. FIG. 1B illustrates possible pathways of magnetization transfer in semi-solid macromolecules and mobile proteins/peptides. The approximate chemical shift range of the proton groups is indicated too. The semi-solid component is treated as a single spin-bath with short a $T_2$ value. All chemical shift values used in this paper are referenced to the water resonance frequency. A variety of spectroscopically distinct proton groups is present in mobile proteins, such as amide protons around 3.6 ppm and aliphatic/olefinic protons covering 0 ppm to −5 ppm. Chemical exchange between exchangeable protons and water is indicated using grey arrows, while the magnetization transfer due to NOE or dipole coupling is indicated using white arrows.

When using sufficiently low $B_1$, effects from direct water saturation (DS) and very fast exchanging protons will be removed by the subtraction, while the effect of slower CEST processes such as for instance APT and rNOE-CEST contrast are preserved and much larger than MTC differences between the two delays. The reason for the latter is that a variable delay will distinguish very short $T_2$ (MTC) and longer $T_2$ species as well as faster and slower transfer processes in long-$T_2$ species. A description of how CEST and rNOE-CEST contrast changes as a function of mixing time in VDMP-CEST experiments for different exchangeable protons in several model compounds (Glu, BSA and cross-linked BSA), followed by a demonstration in vivo in the rat brain is included herein. The MTC contribution can also be removed based on its exchange rate. The scheme requires acquisition of two images: one at a short inter-pulse delay and a second with a longer inter-pulse delay at which the MTC signal is comparable to that at this short delay but for which the CEST transfer processes mentioned above are not. Consequently, subtracting the two images removes MTC.

The present invention can be used to generate images of the transfer of a change in magnetization from mobile species (e.g. proteins) only, and filters out most of the normally dominating semi-solid magnetization transfer effect. The post-RF pulse time delay can be used as a filter for the transfer of magnetization to separate relatively slow exchange processes such as from amide protons or rNOE-CEST from fast exchange processes such as from amine groups, hydroxyl groups. The magnetization buildup curve, i.e. water magnetization change as a function of the waiting delay in VDMP CEST, will provide information on exchange process, and can be used for the detection of physiological or physical properties of the local tissue microenvironment, such as for instance pH. Additionally, the present invention involves collection of two or more images with different delays, one as a reference image and the others (at least one) as a magnetization transfer image for exchanging protons and producing contrast maps from subtracting the images. The resulting images can be weighted by APT, CEST and rNOE-CEST contrast, with the current scheme allowing fast image collection. When using fast imaging and only a single frequency, the sequence becomes insensitive to slow field drifts and scanner instabilities because of the use of a time difference within a brief period.

It should also be noted that the present invention eliminates the need for performing asymmetry analysis in CEST imaging, which is typically done by subtracting effects at lower and higher frequencies with respect to the water resonance in an effort to remove direct saturation and MTC effects, but which is an incomplete procedure because MTC effects themselves are asymmetric with respect to the water frequency. It can distinguish between exchange processes of different speed and thus separate different types of exchanging protons. It removes contributions from direct saturation of the solvent signal. There is minimal interference from magnetization transfer effects from semi-solid and solid tissue components. This technique can provide very short scan times when using a single RF frequency. The method can be translated to clinical MRI scanners to provide many medical MRI applications such as pH mapping, imaging of mobile tissue proteins and peptides, tumor monitoring, and detection of CEST contrast agents.

The magnetization transfer process for water in tissue has contributions from many pools, as illustrated in FIG. 1B. One is the semi-solid macromolecular pool (microsecond $T_2$) giving rise to the conventional MTC effect, another the mobile macromolecular pool of mainly proteins/peptides (millisecond range $T_2$), which, together with many metabolite pools, contributes to the endogenous CEST effect. Due to limited molecular motion, semi-solid protons are coupled strongly via through-space dipole-dipole coupling resulting in spin diffusion between all protons. As a consequence, the $T_2$ is extremely short, on the order of 10 μs for Agar and 50-70 μs for brain tissues. Therefore, the semi-solid pool can be treated as a single proton ensemble or proton bath. The magnetization of this semi-solid pool can be transferred to the water pool via several pathways:

1) Dipolar coupling between bound water and the semi-solid component (Pathway A in FIG. 1B), which is on the order of 50-100 kHz (26) and causes fast magnetization exchange.

Chemical exchange (Pathways B, C and D in FIG. 1B). Some studies suggest that this transfer actually is significant and comparable with the transfer by dipolar coupling if the semi-solid pool includes a large amount of exchangeable protons. The majority of the OH groups (hydroxyl) and $NH_2$ groups (Amine, Cytosine and $NH_3^+$) exchange rapidly with a rate of more than 1 kHz, while the amide and NHNH2 (guanidyl) protons generally exchange slower (<1 kHz).

Thus, the semi-solid component can be treated as a single spin pool with short $T_2$, but different exchange rates as determined by the above transfer pathways. For simplicity, the exchange rate is classified by fast exchange processes, mainly from strong dipolar coupling and fast exchanging protons (OH groups and $NH_2$ groups), and slow/intermediate exchange process from amide protons and guanidyl ($NHNH_2$) groups. Note that fast and slow exchange rates are generally defined with respect to the NMR time scale, which depends on the chemical shift difference between the water and solute protons. The intermediate exchange rate thus applies to this study conducted at 11.7 T, but this could become fast exchange for some pools at lower field strengths such as 3 T. The chemical shift range for the semi-solid pool spans more than 40 ppm (from −20 ppm to 20 ppm with respect to water) for a rat brain, for example. The center frequency of the semisolid pool is determined by the proton density weighted chemical shift of all the protons in the solid pool, which is at the aliphatic frequency for tissues in vivo. It is caused by the large number of aliphatic protons in tissues.

Compared to the semi-solid component, the dipolar coupling and NOEs between protons in mobile macromolecules are much weaker due to the relative fast tumbling of the molecules. The major distinguishing characteristic of mobile protein/lipid components is the millisecond transverse relaxation time of their protons, which can therefore be treated as separate groups, i.e. spectroscopically distinct species. While the magnetization can still transfer via dipolar coupling and NOE cross-relaxation, the magnitude and sign are strongly dependent on molecular dynamics, which is affected by molecular size, viscosity, and binding. The magnetization of the non-exchangeable aliphatic/olefinic and aromatic protons (Pathways H and I in FIG. 1B) can still exchange with water via a two-step process. First, magnetization is transferred from nonexchangeable to exchangeable protons via NOE cross-relaxation and intramolecular dipolar coupling, followed by chemical exchange to water. While the direct dipolar coupling between aliphatic/olefinic/aromatic protons with water contributes significantly to the conventional MTC, this interaction has been shown to be negligible relative to amide proton exchange in mobile proteins. In addition to rNOE-CEST transfer, chemical exchange of directly saturated exchangeable protons contributes to water saturation in mobile species. In conventional APT experiments, the signal is from the relative slow chemical exchange (10-30 Hz (26)) from the amide protons (Pathway E in FIG. 1B). Other proton groups such as the NH2 and OH groups (Pathways F and G in FIG. 1B), which have exchange rates in the range of 700-10000 Hz, contribute only when using very high RF power to saturate them partially before exchange or very long $t_{sat}$ so that very small amounts of saturation can accumulate to become significant.

The VDMP-CEST sequence is illustrated in FIG. 1A. It is similar to the conventional pulsed MTC sequence with a CYCLOPS (CYClically Ordered Phase Sequence) type phase cycle within each block of four 180° pulses. The phase cycle and gradients are applied to destroy residual transverse magnetization (i.e. due to incorrect flip angle and further stimulated echoes) and only longitudinal magnetization transfer was considered. The VDMP-CEST sequence can be used as a $T_2$ filter and magnetization transfer rate filter to distinguish between the signals originating in each of the transfer pathways mentioned above.

Figure 1C:
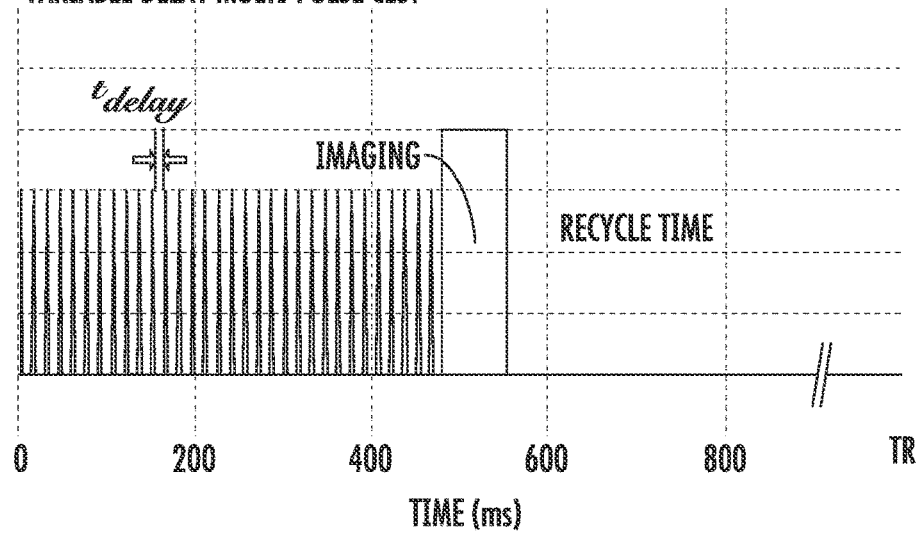
FIG. 1C illustrates another exemplary variable-delay multi-pulse (VDMP-) CEST sequence that can be used to implement the present invention.

FIG. 1C illustrates another exemplary variable-delay multi-pulse (VDMP-) CEST sequence that can be used to implement the present invention. A train of 32 sinc-gauss saturation pulses ($t_{pulse}$=25 ms; 180° each for a $B_1$ of 0.89 µT) is applied at a certain frequency offset followed by a 2D single-shot gradient echo scan (TR/TE/flip angle=14 ms/1.72 ms/12°). This sequence is used in vitro and in vivo in humans to study the rate of saturation buildup for exchangeable protons downfield and NOE-based signals upheld by acquiring Z-spectra as a function of the delay time ($t_{delay}$=1-80 ms) between saturation pulses. This sequence is very similar to the group of selective label-exchange pulse sequences for protons in mobile solutes that have a distinguishable chemical shift. In those approaches, a selective pulse (or a combination of multiple pulses) excites the protons (label) followed by a period of exchange transfer to water. These so-called label-transfer modules (LTMs) are then repeated and signal builds up proportional to the number of labels and the magnetization transfer rate, while it decays with $T_{1w}$. Rapidly exchanging protons will already show the maximum label transfer at short delay, while processes that take longer will show a later maximum. For the current approach in FIG. 1C at the human scanner, the RF pulses (25 ms) are relatively long with respect to the inter-pulse delay and the analytical solution is not straightforward, but the effects can be easily simulated and the experimental data fitted with a 2-pool Bloch model.

Due to the different relaxation properties of the proton pools involved, the RF pulses applied in VDMP-CEST affect them differently. The transverse relaxation time constant, $T_2$, for semi-solid tissue components and larger mobile proteins is short compared to the pulse width (~7 ms here) applied in the VDMP-CEST, respectively. For these, the selective pulses applied at offsets of these systems need to be treated as partial saturation instead of inversion. For highly mobile proton groups in proteins or protons in small peptides or metabolites, $T_2$ values are much longer than the pulses applied in VDMP-CEST and the pulses will be frequency-selective excitation pulses that do not appreciably affect the water protons. A bandwidth of 200-600 Hz was applied in this study in animals and phantoms using the sequence in FIG. 1A at 11.7 T, while the offsets used for amide and aliphatic protons were ±1800 Hz (±3.5 ppm) with respect to the water peak. When using selective inversion, the highest CEST signal will be achieved, namely twice as much as saturation or 90-excite followed by dephasing. The saturation efficiency is described in terms of the absorption lineshape of the protons and the saturation pulse power level $\omega_1$. For the continuous wave situation, the saturation efficiency is $$\lambda = \pi \omega_1^2 g(2\pi\Delta\Omega) \qquad (1)$$

where $\Delta\Omega$ is the frequency offset. The absorption line shape g, is a function of the transverse relaxation time constant of the system, and the integral of the lineshape function is equal to unity. The lineshape of the absorption function has been reported as Gaussian for Agar and Super-Lorentzian for semi-solid biological tissues. The Super-Lorentzian (SL) function is defined as:

$$g(\Delta\Omega, T_2) = \sqrt{\frac{2}{\pi}} \int_0^{\pi/2} \frac{T_2 \sin\theta}{|3\cos^2\theta - 1|} \exp\left(-2\left[\frac{2\pi\Delta\Omega T_2}{\cos^2\theta - 1}\right]^2\right) d\theta \qquad (2)$$

with the difference between the SL and Gaussian functions being that all tissue orientations with respect to the $B_0$ field are integrated. The exact absorption lineshapes for the system with different effective $T_2$ values has been calculated in the literature. Whether a Gaussian or SL function is applied, it can be seen that the saturation efficiency on resonance, i.e. at $\Delta\Omega=0$, is linearly proportional to the effective $T_2$. Then, the saturation efficiency of the semi-solid pool will be several hundred times smaller than the mobile protein/lipid pool for the on resonance situation as seen from their $T_2$ ratio. Consequently, the saturation pulse can be used as a $T_2$ filter to separate the CEST effect from the MT effect if low-power pulses are applied. It is worth noting that the $T_2$ value in Eq. 2 is an effective one, $T_{2,eff}$. Therefore, for the water exchangeable protons, $T_{2,eff}$ is described by $1/T_{2,eff}=k+1/T_2$, where k is the exchange rate. A similar conclusion can be reached from the Bloch equations. The absorption line shape of the free water pool is Lorentzian. In the pulsed CEST sequence of the present invention, the pulse amplitudes are shaped. Deriving an exact analytical solution for the magnetization of the semisolid for a train of shaped pulses is non-trivial. With respect to the present invention, the exchange process was simulated using the Bloch equations without applying the above approximations, i.e. simulating the saturation effect of the Gaussian pulses. The saturation power indicated in the work is the peak power of the Gaussian pulses.

Figure 2:
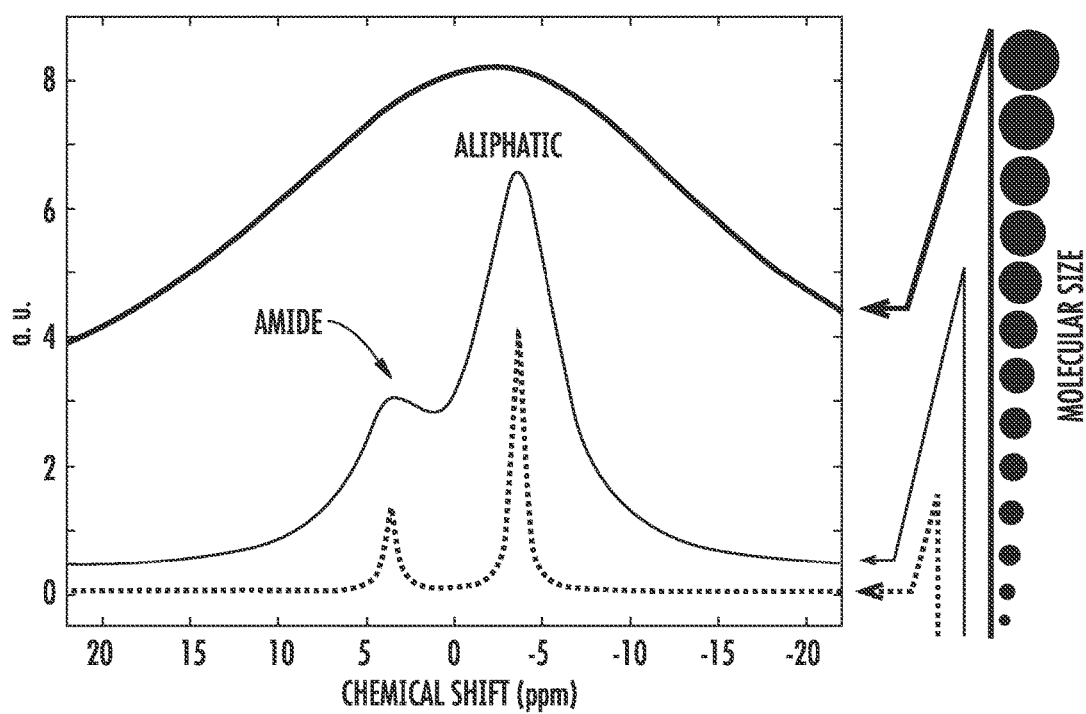
FIG. 2 illustrates magnetization transfer (MT)/CEST spectra from proteins/lipids with different mobility, i.e. different $T_2$ values.

In tissues, there is a broad distribution of $T_2$'s due to different molecular sizes and concomitant mobilities of the protons in the proteins/lipids, ranging from 0.008 ms to 26 ms in myelin lipids and probably up to 100 ms in more mobile peptides and metabolites. When varying the power of the pulses applied in VDMP-CEST, protons with different $T_2$ values will experience different saturations, which is illustrated in FIG. 2. It should be noted that the line broadening effect introduced by the direct saturation of the pulses is neglected in this simulation. For weak pulses, only the mobile proteins are saturated and the amide and aliphatic/olefinic proton peaks will be spectroscopically distinguishable at offsets of about ±3.6 ppm respectively, which is the case observed in CEST experiments. With increased saturation power, more and more proteins/lipid protons with short $T_2$ values will be saturated, which causes the two proton groups (amide and aliphatic/olefinic) to start overlapping. Eventually the two groups will merge into a single broad peak at strong power, which is the case observed in conventional MTC experiments. From this simulation, it can be seen that the VDMP-CEST approach can target different proton groups, in contrast to the MTC experiment. To accomplish this, the saturation power has to be low enough to avoid overlap of the proton groups, but sufficiently high for measurable effects. 4 µT (200 Hz bandwidth) Gaussian pulses were a proper choice at 11.7 T, allow separation of APT signal from rNOE-CEST, while still maintaining reasonable signal to noise ratio. The simulation also explains the observation by others that a strong rNOE-CEST is observed for lower power (<2 µT) continues wave saturation CEST pulses, while the rNOE CEST will disappear at strong saturation power due to the dominance of the aliphatic/olefinic peaks of semisolid protons. Further FIG. 2 illustrates MT/CEST spectra from proteins/lipids with different mobility, i.e. different $T_2$ values. In the plot, the strong water signal is not shown for clarity. When weak RF pulses are applied in VDMP-CSET, the CEST spectrum arises mainly from mobile proteins/lipids with long $T_2$ values and the amide and aliphatic/olefinic peaks are two well separated groups (dotted green line). When higher saturation power is applied, more and more large molecules will be observed, and the amide and aliphatic peaks will overlap partially (dashed line). The CEST signal is not specific any more. At the strong saturation power extreme, almost all protons are observed including some with very short $T_2$ value, and the VDMP-CEST spectrum will be a single broad line including both the amide and aliphatic protons (solid line). The spectrum becomes the convential MTC signal. In the simulation, the line broadening due to direct saturation was not included.

Under the assumption of a two-pool exchange model, the magnetization transfer process observed for a pulsed MT/CEST sequence will show two phases in time, namely saturation buildup and decay with $T_1$ of water ($T_{1w}$) and, for high concentration of protons, due to the back exchange process. The equilibrium time point depends upon the relative rate constants of transfer and relaxation. For very fast transfer, the magnetization exchange already happens during the pulse time ($t_p$). The buildup/decay process for a VDMP-CEST sequence resembles the situation when using label transfer modules (LTMs), similar to the frequency-labeled exchange (FLEX) sequence. In the VDMP-CEST, the pulse performs labeling while transfer occurs during the mixing time ($t_{mix}$). Therefore, an analytical equation can be used to describe the proton transfer ratio (PTR) under the assumption that the combined label and transfer period ($t_p+t_{mix}$) is much smaller than T1w and the exchange rate (k) is slow enough for exchange during the pulses ($t_p$) to be neglected.

$$PTR = x \cdot \lambda \cdot \eta \cdot \beta \quad (3a)$$

$$\eta = \sum_{i=1}^{n} e^{-nt_{mix}/T_{1W}} \quad (3b)$$

$$\beta = 1 - e^{-k \cdot t_{mix}} \quad (3c)$$

Where x is the concentration ratio between exchangeable and water protons, $\lambda$ is the saturation efficiency (Eq. 1) and $\beta$ the exchange transfer efficiency. The PTR is further determined by the sum of the magnetizations transferred by the n pulses. In the equation, the efficiency factor $\beta$ describes the buildup process and is effectively an exchange filter. Equation 3 is useful to understand the idea of saturation buildup with k and decay with $T_{1w}$, and illustrates how the sequence is an exchange filter. However, for the long pulse widths used here (3-7 ms) in VDMP-CEST, Eq. 3 will be suitable only for extremely slow exchange processes. To be exact for the wide range of exchange rates covered here, therefore the exchange process was simulated using the Bloch equations. The above theory suggests that APT and rNOE-CEST can be separated from MTC and other effects when combining proper pulse powers ($T_2$ filter) and pulse delays (magnetization transfer rate filter) in VDMP-CEST. The proposed fast method for APT and rNOE-CEST MRI in the current work consists of recording two images with two pulse delays, one with zero mixing time and another at the mixing time where the equilibrium APT-CEST or rNOE-CEST saturation is reached. Then, the APT or rNOE aliphatic CEST can be obtained by subtracting the two images. By using a low pulse power and less pulse numbers, the MTC and very rapidly exchange protons will be only weakly saturated (see FIG. 2). When subtracting the two images, these two contributions will reduce even more (close to negligible) and the direct water saturation will be removed. An APT image obtained this way (irradiation at 3.5 ppm and varying the delay) is therefore expected to be free of interference from MTC asymmetry, amine and hydroxyl proton contributions and, since no asymmetry analysis is done, from rNOEs from aliphatic protons. Therefore, it is referred to as clean-APT to distinguish it from the traditional APT method based on $MTR_{asym}$ determination.

EXAMPLE

An exemplary implementation of the present invention is described herein, in order to further illustrate the present invention. The exemplary implementation is included merely as an example and is not meant to be considered limiting. Any implementation of the present invention on any suitable subject known to or conceivable by one of skill in the art could also be used, and is considered within the scope of this application.

MRI experiments were performed on a horizontal 11.7 T Bruker Biospec system equipped with actively shielded gradients of maximum strength 74 Gauss/cm. Experiments on phantoms were performed using a 23 mm volume transceiver coil (Bruker) at room temperature. The image acquisition was achieved using a fast spin-echo (FSE) sequence with TR/TE=13 s/4 ms, NA=1, 50 kHz receive bandwidth, slice thickness 1 mm, and 32×32 image matrix (FOV 2×2 cm$^2$). In the VDMP-CEST sequence, depending on the application, 4-64 Gaussian shaped RF pulses (180 degree flip angle) were applied during preparation. Pulse powers of 4 μT (6.9 ms, 200 Hz bandwidth) and 12 μT (2.3 ms, 600 Hz bandwidth) were used. A Z-spectrum was recorded from −7 ppm to 7 ppm in steps of 0.4 ppm. An S0 image was recorded by setting the irradiation offset to 200 ppm.

For the rat study, a 72 mm quadrature volume resonator (Bruker) was used for transmission and a 2*2 phased array coil (Bruker) for reception. CEST images were acquired using a FSE readout with TR/TE=6 s/4 ms, NA=1, slice thickness 1 mm, and 64×64 matrix (FOV 1.8×1.8 cm$^2$); 8 Gaussian shaped RF pulses (180 degree flip angle) with peak powers ranging from 2 μT ($t_{pulse}$=13.8 ms) to 12 μT ($t_{pulse}$=2.3 ms) were used for recording the VDMP-CEST images. The Z-spectrum was recorded from −20 ppm to 20 ppm. The proper pulse delay $t_{mix}$ and the number of saturation pulses was selected by acquiring the water saturation as a function of delay time and determining the equilibrium point between transfer buildup and relaxation decay. The B0 field over the rat brain was adjusted using the field mapping and shimming up to second order. The quality of the shim was examined using WASSR method.

Three samples representing different mobility molecules in tissues were used to demonstrate the VDMP-CEST sequence. Mobile proteins in tissue were mimicked by a Bovine Serum Albumin (BSA, 66.5 kDa, Sigma-Aldrich A2058) protein solution. A BSA solution (10% by weight; 1.5 mM; pH=7.3) was prepared and placed in a 5 mm NMR tube. Semi-solid proteins in tissue were modeled using a cross-linked 10% BSA sample at pH 7.3. Cross-linking was achieved by heating the solution in a 80-90° C. water bath for 30 minutes after which a transparent gel-like sample was formed. The cross-linked BSA sample showed strong dipolar coupling similar to the traditional MTC phantom (agar).

A glutamate (Glu) solution was used to model small metabolites in tissue, particularly the amine group commonly found in proteins and metabolites, the exchange of which competes with the amide protons and the chemical shift range of which overlaps due to exchange broadening. A 12.5 mM Glu (Sigma-Aldrich, G1251) solution was prepared in PBS to pH=7.3. The chemical shift of the amine proton was 2.5 ppm. The exchange rate at this pH was previously measured to be 5500 kHz.

Five adult male Wister rats weighting 280 to 320 g were anesthetized using 5% isoflurane in a 75%/25% air/oxygen mixture, followed by 2% to 2.5% isoflurane during the MRI scan. The rat head was immobilized by a bite bar and two ear bars. During scanning, rats were placed on a water heated animal bed equipped with temperature and respiratory control. Respiration was monitored and maintained at 20-30/min. After the scans, the anesthetized rats were sacrificed by injection of saturated KCl.

Figures 7A, 7B:
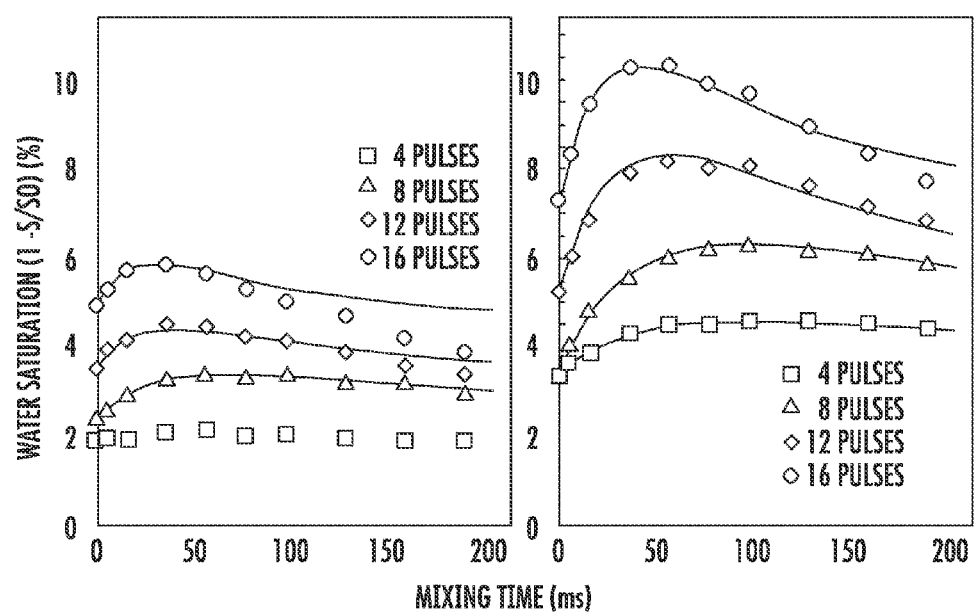
FIGS. 7A and 7B illustrate saturation buildup curves in rat brain cortex obtained using VDMP-CEST sequence at offsets of 3.6 ppm, as in FIG. 7A, and −3.6 ppm, as in FIG. 7B.

The saturation buildup curves of the phantoms and rat brain recorded using the VDMP-CEST sequence were fitted using a two-pool Bloch model. The $T_2$ and $T_1$ values for the exchangeable proton were set to typical literature values, and are listed in the figure captions. The $T_2$ values for the water pool ($T_{2w}$) on phantoms were measured by CPMG experiments ($T_{2w}$=110 ms, 108 ms and 78 ms for Glu, BSA solution, and cross-linked BSA, respectively), while the $T_{2w}$ of rat brain was set to the literature value at this field, i.e. $T_{2w}$=36 ms. The fitting parameters were the effective $T_1$ of water ($T^*_{1w}$), exchangeable proton fraction with respect to water proton concentration (x), exchange rate (k) and one constant offset due to direct saturation (DS). DS varies with frequency offset, but is a constant value with respect to the mixing time at a particular frequency offset. The value of $T_{2s}$ is difficult to be measured experimentally. In the fitting, however, it was found that the exchange rates and the shape of saturation buildup curves were not sensitive to the values of $T_{2w}$ and $T_{2s}$, allowing the proper determination of exchange rates from fitting these curves. The maximum saturation level in the saturation buildup curves is determined by the exchangeable proton fraction x. However, the accuracy of x is significantly affected by the uncertainty of the $T_{2w}$ and $T_{2s}$, since the saturation efficiency is related to the $T_{2s}$ as seen from Eq. 1. In the fitting, the back exchange process is automatically accounted for in the Bloch equations (see simulation in FIG. 3B). The $T^*_{1w}$ values are smaller than $T_{1w}$ due to the interference of MTC and other saturation and saturation transfer processes. The interference will be more obvious for higher pulse numbers or when a large MTC pool is present, as seen in the fitting on rat brain (FIGS. 7A, B). Notice that a 1.5 mM protein may have hundreds of mM of protons.

Figure 3A:
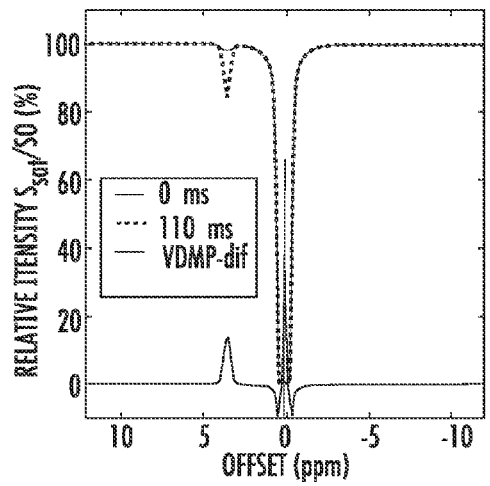
FIGS. 3A-3D illustrate simulated Z-spectra and saturation buildup curves for a VDMP-CEST sequence (6.9 ms pulses of $B_1$=4 μT) using two-pool Bloch equations (20 mM amide pool: $T_{1s}$=1 s, $T_{2s}$=20 ms; water pool: $T_{1w}$=2 s and $T_{2w}$=35 ms).
Figure 3B:
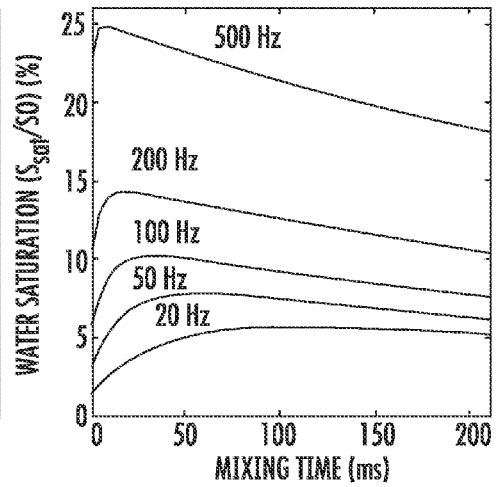
Figure 3C:
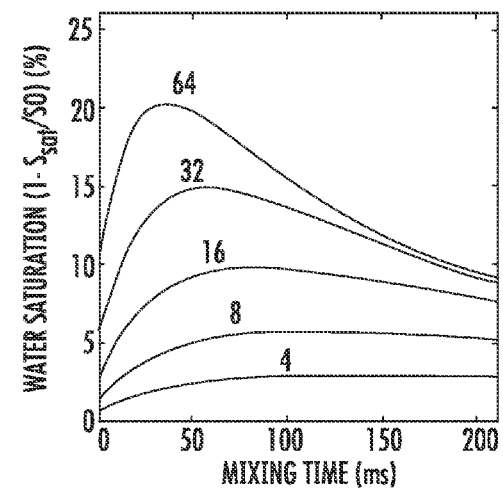
Figure 3D:
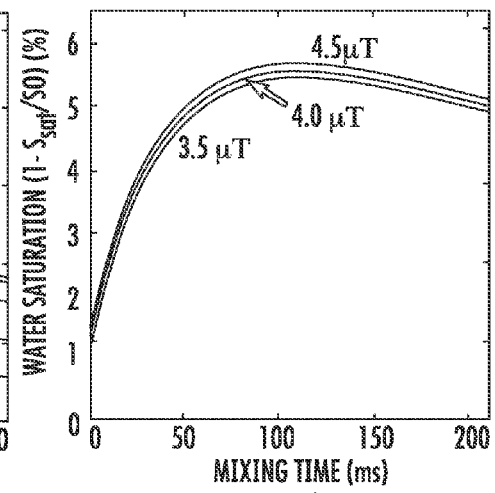

In FIGS. 3A-D, the results of Bloch simulations for 20 mM of amide protons in water are shown for the VDMP-CEST sequence of FIG. 1A using $B_1$=4 μT and $t_{pulse}$=6.9 ms (200 Hz bandwidth). FIG. 3A shows Z-spectra when using 8 pulses and mixing times of 0 ms and 110 ms for an exchange rate of 20 Hz. The VDMP difference spectrum around 3.5 ppm shows only the amide proton peak and is a clean-APT spectrum. The direct saturation effect due to the Gaussian pulses is canceled out at this frequency, because it is determined by the pulse length and strength and not the inter pulse delays that are short with respect to $T_{1w}$. At 0 ppm the DS cancellation is not perfect due to the large size of the effect and some T1w recovery becoming measurable. FIG. 3B shows the saturation buildup curves as a function of mixing time for exchange rates ranging from 20 Hz to 500 Hz. For the very rapidly exchanging protons, the saturation already reaches equilibrium during the saturation pulses, i.e. for inter-pulse delays of zero, which is expected to be the case for most amine and hydroxyl protons. Therefore, varying the mixing time will not increase the CEST signal for such fast exchanging protons if the water relaxation time is sufficiently long. For these fast exchanging protons, the water saturation is a substantial fraction of $S_0$ and saturation transfer back from water to the exchangeable protons, i.e. the back exchange effect, will occur. As a consequence, the CEST signal will decay faster with an apparent rate $1/T^*_{1w}$=$1/T_{1w}$+$x_s k$, where x is the fraction of exchangeable proton. When eight pulses are applied, the equilibrium water saturation for slowly exchanging amide protons (k=20 Hz) is still small (a few percent) and the equilibrium between buildup and decay is reached at longer mixing time (110 ms). Therefore, the inter-pulse delay time, $t_{mix}$, can be used as a filter for different exchange rates. The effect of number of saturation pulses is simulated in FIG. 3C. When the number of pulses is very high, the saturation maximum is reached at lower mixing time, which is again due to a large back exchange effect when a substantial fraction of the water pool is saturated. On the other hand, a low pulse number will lead to less CEST signal enhancement. The selection of the proper pulse number is thus determined by the concentration of exchangeable protons, and their exchange rates. In current simulation, the APT signal difference between zero mixing time and the time at which equilibrium between buildup and decay occurs was maximized for about 8 pulses with $B_1$=4 μT. In order to test whether $B_1$ inhomogeneity affects the build-up curve, the buildup was simulated for $B_1$=4 μT with a 0.5 μT error. The curves are similar, but show that the sequence has some $B_1$ dependency.

Figures 4A, 4B:
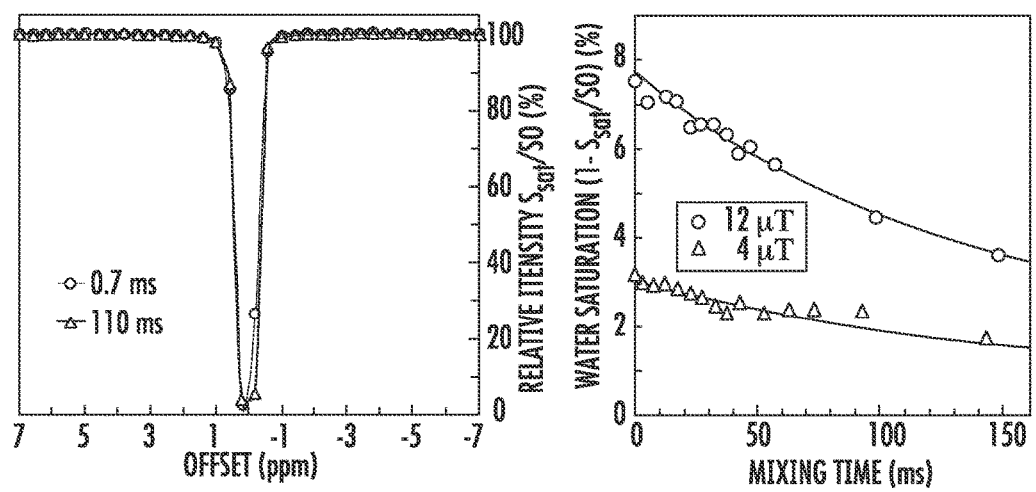
FIG. 4A illustrates experimental VDMP-CEST Z-spectrum for a glutamate phantom (12.5 mM, pH=7.3) in PBS.
FIG. 4B illustrates an experimental VDMP-CEST build-up curve at a frequency of 2.5 ppm for the glutamate.

FIG. 4A shows Z-spectra for the 12.5 mM Glu solution recorded using an 8-pulse VDMP-CEST sequence with $B_1$=4 μT ($t_p$=6.9 ms) and mixing times of 0.7 ms and 110 ms. The Z-spectrum was identical to one recorded on PBS (data not shown). It can be seen that amine protons with fast exchange rates cannot be observed with such a low pulse number and power, even at long mixing time. Under these experimental conditions, the interference from amine protons would be removed completely when recording APT images. When increasing the number of pulses to 32, a small effect become visible at 4 μT (FIG. 4B) and when increasing $B_1$ a clear mixing time dependence becomes visible, but this is a decay contrary to a buildup, similar to the simulation results (FIG. 3B) when comparing fast versus slowly exchanging protons.

Figure 5A:
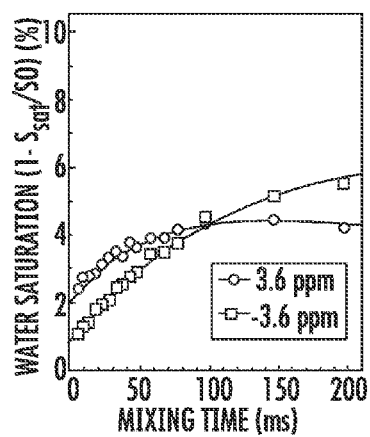
FIGS. 5A and 5B illustrate saturation buildup curves for 10% BSA in solution (A) and cross-linked (B) obtained using a VDMP-CEST sequence with 8 Gaussian pulses and $B_1$=4 μT (200 Hz bandwidth).
Figure 5B:
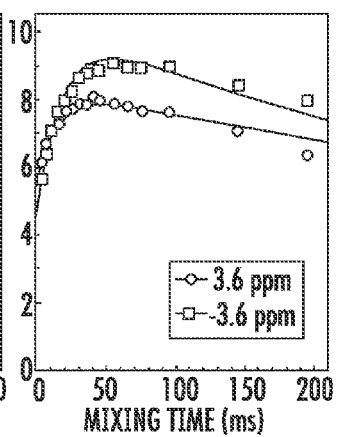
Figure 5C:
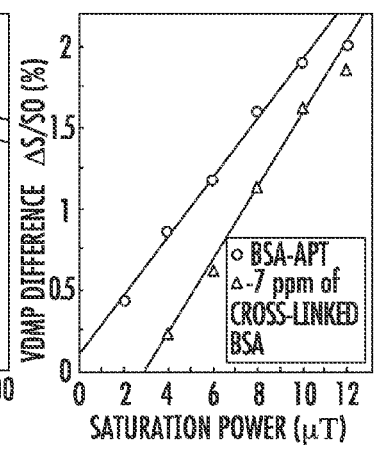
FIG. 5C illustrates saturation power dependence for an 8-pulse VDMP-CEST difference signal intensity (between $t_{mix}$=110 ms and 0.7 ms) at offsets 3.6 ppm (APT) and −7 ppm (MTC background signal).

The saturation buildup curves for the BSA solution and cross-linked BSA at offsets of 3.6 ppm and –3.6 ppm using 8 pulses of 4 μT power are plotted in FIGS. 5A and 5B, respectively. The solid lines are the curves fitted using the two-pool Bloch equations with $T_{1s}$ and $T_{2s}$ assumed as indicated in the Figure legend. The amide proton exchange rate ($k_{NH}$) of the BSA solution at room temperature was found to be 13 Hz, while the aliphatic magnetization transfer rate ($R^{rNOE}$) was only 3 Hz. Once the BSA protein was cross-linked (FIG. 5B), the buildup curves at both –3.6 ppm and 3.6 ppm changed significantly compared to the BSA solution in that the curve shapes became similar for the amide and aliphatic offsets, as reflected in the rates $k^{NH}$=60 Hz and $R^{rNOE}$=50 Hz. This confirms that the cross-linked BSA can be treated as a single proton pool with an exchange rate that is similar for each offset and amounts to the average from all exchange processes, including dipolar coupling and proton exchange. The effect of peak saturation power (note that bandwidth varies as pulses are always 180°) on the amide proton pool (BSA-APT) and MTC pool (Cross-linked BSA) is demonstrated in FIG. 5C for an 8-pulse sequence. Here the signal at offset –7 ppm was used to study MTC in order to avoid potential interference from highly mobile side chain amide and aliphatic protons in crosslinked BSA. The VDMP saturation difference signals for both MTC and BSA-APT signals were proportional to the saturation power. For these experimental conditions, a saturation power lower than 4 μT would be sufficient to suppress the MTC interference.

Figure 6A:
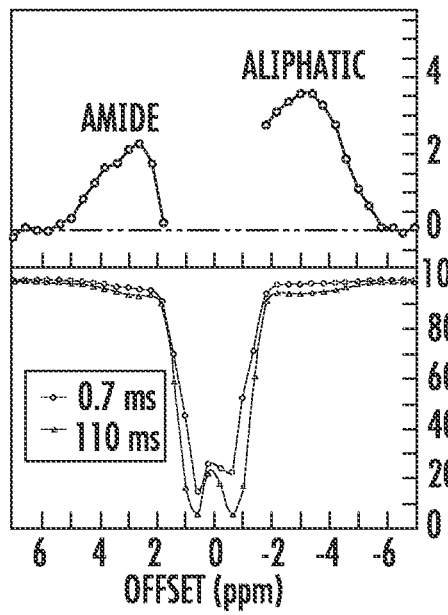
FIGS. 6A-6D illustrate mixing-time dependent Z-spectra (bottom) and corresponding VDMP-CEST difference spectra (top) for 10% BSA in solution, as in FIGS. 6A and 6B, and cross-linked, as in FIGS. 6C and 6D, obtained using a VDMP-CEST sequence with 8 Gaussian inversion pulses.
Figure 6B:
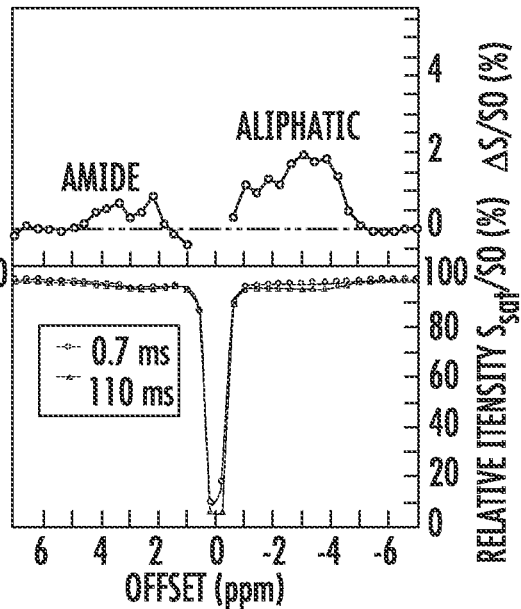
Figure 6C:
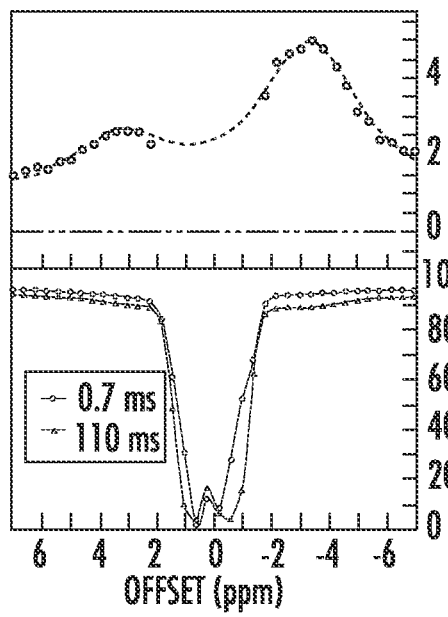
Figure 6D:
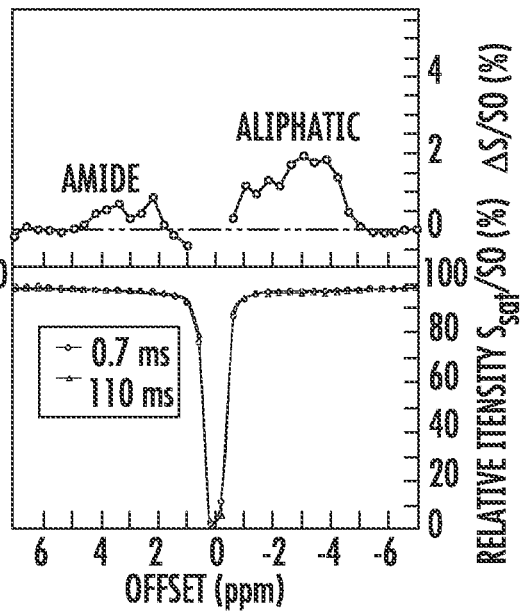

In FIGS. 6A-6D, 8-pulse VDMP-CEST data for BSA solution (FIGS. 6A, B) and crosslinked gel (FIGS. 6C, D)

are shown for $B_1$-levels of 12 µT (FIGS. 6A,C) and 4 µT (FIGS. 6B,D). Each dataset shows Z-spectra recorded at two mixing times (bottom) and the corresponding VDMP difference spectrum (top). At the minimum 0.7 ms mixing time in solution, there is only a very small saturation effect in the upheld region in the Zspectrum, i.e. the aliphatic proton range, while there is already a broad saturation dip downfield (around 2-5 ppm) attributed to the rapidly exchanging amine protons centered around 2.2 ppm when in the intermediate exchange regime. This strong saturation of the amine protons will complicate clean detection of the amide protons when using traditional asymmetry analysis. With the variable delay approach, however, the two proton types can be separated based on their significantly different exchange rates (FIGS. 6A, B). As demonstrated in the simulations (FIG. 3B) and the Glu experiments (FIGS. 4A, B), the CEST effect from rapidly exchanging protons does not increase with mixing time since their transfer is already accomplished during the pulses. The VDMP-CEST difference spectra in FIGS. 6A and B therefore show effects only from slowly transferred saturation, such as for chemical exchange of amide protons at 3.5 ppm, and relayed NOEs for aliphatic protons in the upfield range. The integral of the aliphatic CEST signal is more than double the APT signal. The CEST spectrum at lower saturation power can be measured over a somewhat larger spectral range closer to water, due to the fact that less direct saturation occurs. When 4 µT (200 Hz bandwidth) inversion pulses are used, the bandwidth is lower than for 12 µT (600 Hz bandwidth), resulting in weaker CEST and rNOE effects. However, the VDMP difference spectrum recorded with 4 µT pulses has much higher resolution (FIG. 6B).

For the cross-linked BSA sample, the Z-spectra and VDMP difference spectra differ significantly from those in solution. The amide proton dip (2-5 ppm) in the Z-spectrum is difficult to distinguish because the strong dipolar coupling among all protons leads to a broad solid-like spectrum. The VDMP difference spectrum is not as well defined as for solution, but broader due to the strongly coupled matrix. The $T_2$ of the cross-linked BSA protons was estimated by fitting the lineshape of the VDMP difference spectrum assuming pools from one aliphatic group and one amide group only. This resulted in a $T_{2w}$ of 130 µs and the proton density ratio aliphatic:amide of 2.5:1. It is notable that this $T_{2w}$ value reflects the averaged proton relaxation time of the protons saturated with peak power 12 µT. The measured $T_{2w}$ values will become shorter when applying higher power saturation pulses. When using 4 µT pulses (FIG. 6D), the difference spectrum only shows a slight signal decrease in the exchangeable proton region downfield, which is due to the $T_1$ recovery of water during the mixing time. A small increase is still visible upfield, which may arise from side chains of the proteins with higher mobility. A comparison to the VDMP difference spectrum in BSA solution (FIG. 6B) suggests that a series of 8 Gaussian inversion pulses of 4 µT strength should be able to separate the amide and amine protons in mobile proteins from the semi-solid pool, while the majority of any upfield effect should be from mobile proteins.

The saturation buildup curves for rat brain cortex are plotted as a function of number of inversion pulses in FIG. 7. The buildup curves are similar to the simulation in FIG. 3C. As expected, the APT/rNOE effect will be enhanced by more pulses, but be the maximum enhancement is limited by $T_{1w}$ and back exchange. The latter is described by $x_s k$, and may thus result either from the high concentration amide/aliphatic protons or from lower concentration fast exchanging protons. The back exchange process, involves all saturated water protons (i.e. amides will have interference from MTC and amines) and will cause quick decay of the saturation buildup curves when the amount of saturated protons reaches a substantial fraction of the water signal. From the buildup curves, it can be seen that 8 pulses is an excellent choice for $B_1$=2 µT, achieving enough enhancement of APT/rNOE while minimizing interference from MTC and other fast exchange protons. For this number of pulses, the saturation reaches steady state at around 110 ms for aliphatic and amide protons. When fitting all buildup curves combined (multi variate), amide proton and rNOE exchange rate, rates of 30 Hz and 17 Hz were found, Here, 2 µT saturation power was chosen to make sure that the interference from MTC and amine protons was fully suppressed. When performing a similar experiment for $B_1$=12 µT (600 Hz), the 8 pulse sequence was also the optimized condition, reaching a saturation steady state at 110 ms for both amide and aliphatic protons (data not shown).

In FIGS. 8A-F, VDMP-CEST spectra for healthy rat brain cortex acquired using saturation pulses of 12 µT, and 2 µT are plotted for two mixing times. At 12.0 µT, the VDMP difference spectra illustrate the $T_2$ filter effect of the Gaussian saturation pulses. In the VDMP spectra recorded with low power pulses, the amide/aliphatic peaks are better resolved but have lower signal to noise (~5 times lower).

Figure 9A:
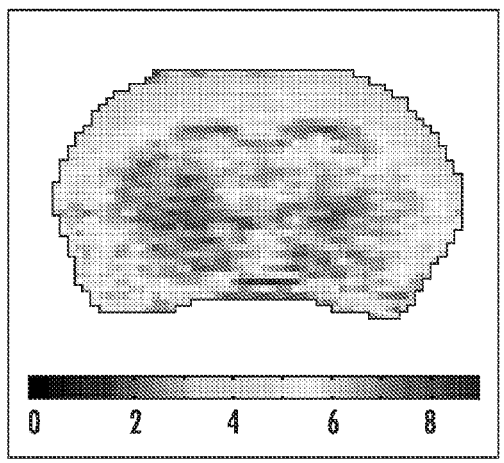
FIGS. 9A-9D illustrate VDMP-CEST difference images of rat brain recorded using different offsets.
Figure 9B:
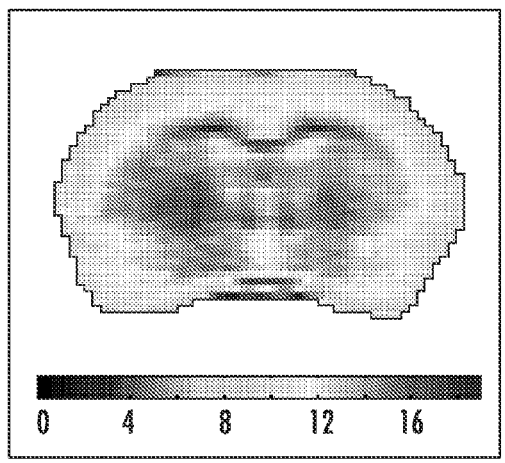
Figure 9C:
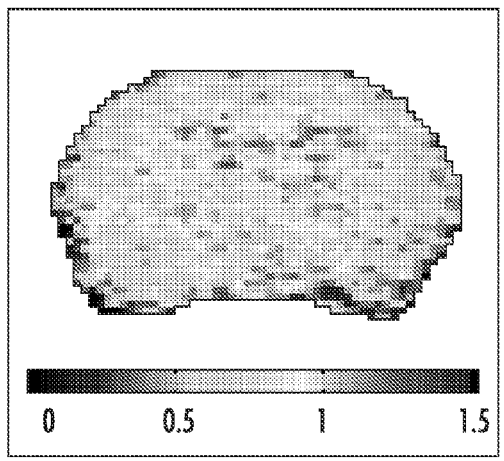
Figure 9D:
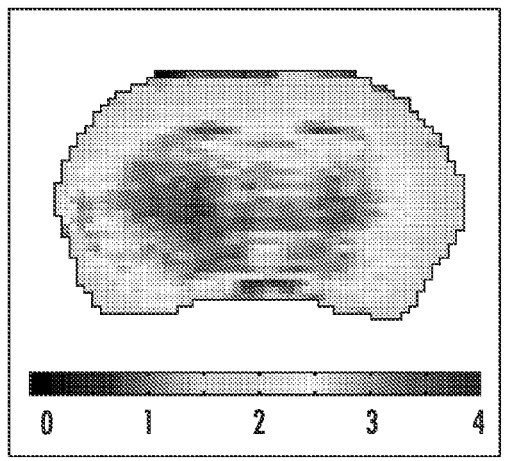

APT and rNOE VDMP difference images of a rat brain acquired using 2 µT and 12 µT pulses are shown in FIGS. 9A, B and FIG. 9C, D, respectively. At the lower peak power of 2 µT, the images at offsets 3.6 ppm (FIG. 9C) and −3.6 ppm (FIG. 9D) differ appreciably and most likely reflect clean-APT and rNOE-CEST effects. Both Clean-APT and rNOE-CEST of the muscle of the rat are significantly lower than the values of the brain.

Figures 10A, 10B, 10C, 10D, 10E, 10F:
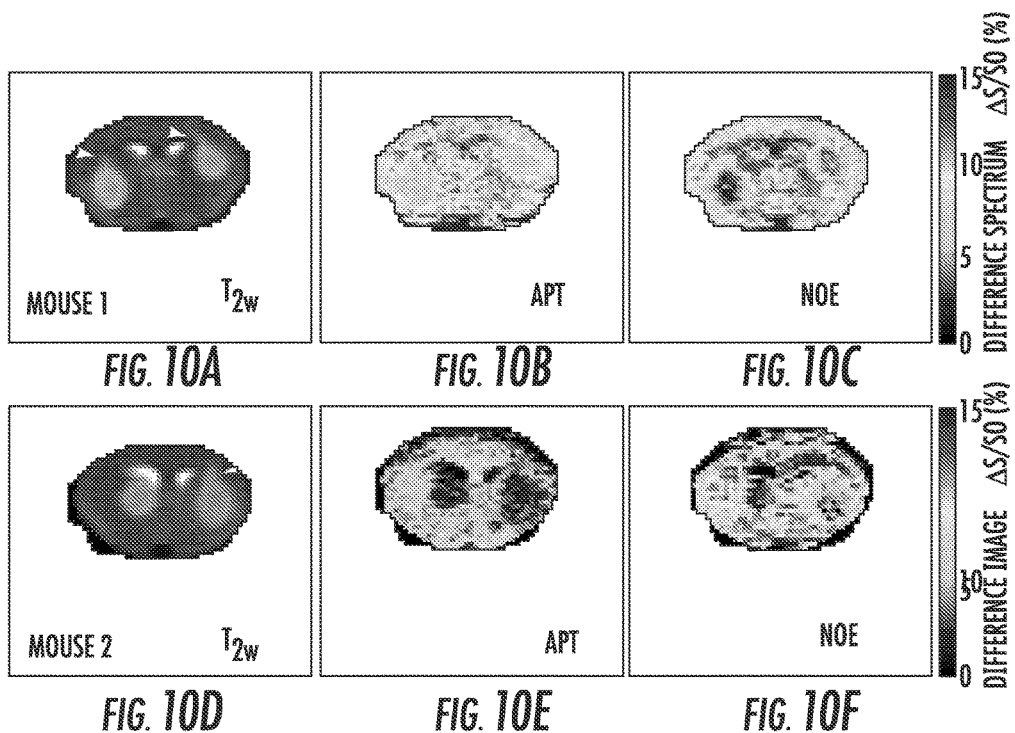
FIGS. 10A-10F illustrate VDMP-CEST difference images of mouse brain recorded on two mice with 9 L-gliomas.

FIGS. 10A-F illustrate VDMP-CEST difference images of mouse brain recorded on two mice with 9 L-gliomas. 200,000 cells (in 2 uL) were injected to induce the glioma, and the images were recorded one week after injection. The $T_2$ weighted images, recorded using a RARE MRI pulse sequence with 40 ms echo time, are presented in FIGS. 10A and 10D. The VDMP-CEST images were recorded using 8 labeling pulses (each with $B_1$=12 µT, 600 Hz bandwidth) at offsets 3.6 ppm (FIGS. 10B and 10E) and −3.6 ppm (FIGS. 10C and 10F). The final APT-CEST and rNOE-CEST images in all experiments were obtained by (i) acquiring ΔS images at 0.7 ms and 110 ms mixing time, (ii) taking the difference between these images, (iii) and finally normalizing the difference image by an $S_0$ image. Both APT-CEST and rNOE-CEST images provide good contrast on the gliomas and this contrast is different compared to the $T_{2w}$ images. Some bright spots close to the gliomas which are caused by the needle surgery (see the white arrows) are not seen in the NOE-CEST images. Therefore, the APT-CEST and NOE-CEST methods may provide more specific information on the tumor size, tumor type, and tissue damage.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for detecting the buildup of exchange transfer processes from nuclei in endogenous or exogenous mobile solute molecules in tissue using magnetic resonance (MR) imaging comprising:
   applying a series (one or more) of radiofrequency pulses to change a magnetization of one or more MR sensitive nuclei in the endogenous or exogenous mobile solute molecules;
   waiting a period after each pulse for transfer of the magnetization change to another one of the endogenous or exogenous mobile solute molecules;
   detecting this another one of the endogenous or exogenous mobile solute molecules using MR imaging or spectroscopy;
   repeating the applying of the series of radiofrequency pulses to change the magnetization of one or more MR sensitive nuclei in the endogenous or exogenous mobile solute molecules;
   waiting a different period after each pulse for a transfer of a different magnitude of magnetization change to occur to another one of the endogenous or exogenous mobile solute molecules;
   detecting the another one of the endogenous or exogenous mobile solute molecules using MR imaging or spectroscopy; and
   determining a difference MR signal for the another one of the endogenous or exogenous mobile solute molecules between the applications of the pulses with different waiting period.

2. The method of claim 1 wherein the mobile molecules are characterized by having a finite linewidth, i.e. excluding semi-solid molecules studied in conventional magnetization transfer contrast (MTC).

3. The method of claim 1 wherein the radiofrequency pulse is a frequency-selective excitation pulse for chemical shift(s) of the nuclei of interest.

4. The method of claim 1 wherein a radiofrequency pulse is a frequency-selective saturation pulse for the chemical shift(s) of the MR sensitive nuclei.

5. The method of claim 1 wherein the MR sensitive nuclei can be any nucleus that has spin and thus is detectible with magnetic resonance, for instance 1H, 13C, 31P, 23Na, and all nuclei used for NMR and MRI.

6. The method of claim 1 wherein the period for waiting after each pulse is as short as 0 ms for the first pulse sequence and range from 1 to several hundred ms for the repeating the applying of the radiofrequency pulse.

7. The method of claim 1 wherein the transfer of the magnetization change occurs directly via chemical exchange after labeling of an exchangeable nucleus.

8. The method of claim 1 wherein the transfer of the magnetization change occurs in a relayed fashion via magnetization of other nuclei in the molecule.

9. The method of claim 1 wherein the transfer of the magnetization change occurs via exchange of a multi-atomic entity containing a labeled magnetic nucleus or nuclei via other nuclei.

10. The method of claim 1 wherein the another molecule is a solvent.

11. The method of claim 1 wherein the another molecule is another solute.

12. The method of claim 1 wherein the repeating of the pulse sequence is at least once.

13. The method of claim 1 wherein the waiting a period and waiting a different period comprises different repeats when doing more than one repeat.

14. The method of claim 1 wherein a change in magnitude of the magnetization transfer is studied as a function of waiting time after the radiofrequency pulses or by taking the difference between different waiting times.

15. The method of claim 1 wherein the magnetization transfer from other protons with different exchange rates can be suppressed by taking the difference between different waiting times, where the magnitude of the signal of other protons are equal at the two waiting times.

16. The method of claim 1 wherein the mobile solutes are selected from a group consisting of endogenous or exogenous peptides, proteins, carbohydrates, metabolites or exogenous contrast agents.

17. The method of claim 8 wherein the relay is accomplished using nuclear Overhauser enhancement (NOE) or dipolar transfer.

18. The method of claim 14 wherein the change in magnitude is used to determine magnetization transfer rates or exchange transfer rates of the nuclei or molecular moieties involved.

19. The method of claim 14 wherein the change in magnitude is used to monitor pH of the tissue.

20. The method of claim 1 further comprising a magnetic resonance processor set up to process and display the waiting time dependent signals and the changes therein.

21. The method of claim 1 further comprising acquiring magnetization changes as a function of waiting time at multiple frequencies.

22. The method of claim 21 further comprising studying the change in magnitude of the magnetization transfer at each of the multiple frequencies as a function of waiting time after the radiofrequency pulse or by taking the difference between different waiting times.

23. The method of claim 22 wherein the time-dependent magnetization difference is compared between different frequencies or studied as a function of frequency.

24. A non-transitory computer readable medium programmed with elements comprising:
   acquiring magnetic resonance image data of a subject;
   applying radiofrequency pulses with different time delays to alter the magnetic resonance image data of the subject;
   applying time-dependent pulse sequence at multiple selective frequencies to alter the magnetic resonance image data of the subject;
   analyzing a difference in magnetization change as a function of waiting time;
   generating and displaying images of the differences in magnetization change as a function of waiting time; and
   generating and displaying different images of the images acquired of the differences in magnetization change as a function of frequency.

* * * * *